United States Patent
Kayo et al.

(10) Patent No.: US 9,434,744 B2
(45) Date of Patent: Sep. 6, 2016

(54) LOW TEMPERATURE SYNTHESIS OF RAPAMYCIN DERIVATIVES

(71) Applicant: BIOSENSORS INTERNATIONAL GROUP, LTD., Hamilton (BM)

(72) Inventors: Margaret W. Kayo, Los Altos, CA (US); Richard S. Fornicola, Devens, MA (US); Ivan Kovacik, Devens, MA (US)

(73) Assignee: Biosensors International Group, Ltd., Hamilton (BM)

( * ) Notice: Subject to any disclaimer, the term of this patent is extended or adjusted under 35 U.S.C. 154(b) by 0 days.

(21) Appl. No.: 14/804,714

(22) Filed: Jul. 21, 2015

(65) Prior Publication Data
US 2015/0322086 A1  Nov. 12, 2015

Related U.S. Application Data

(63) Continuation of application No. PCT/US2014/012398, filed on Jan. 21, 2014.

(60) Provisional application No. 61/755,388, filed on Jan. 22, 2013.

(51) Int. Cl.
*C07D 498/18* (2006.01)
*C07D 498/04* (2006.01)

(52) U.S. Cl.
CPC ........... *C07D 498/18* (2013.01); *C07D 498/04* (2013.01)

(58) Field of Classification Search
CPC ................................................. C07D 498/18
See application file for complete search history.

(56) References Cited

U.S. PATENT DOCUMENTS

| | | | |
|---|---|---|---|
| 7,193,078 B2* | 3/2007 | Isozaki | C07D 498/18 540/456 |
| 7,220,755 B2* | 5/2007 | Betts | C07D 498/18 514/291 |
| 7,812,155 B2* | 10/2010 | Kawanishi | B01D 15/322 540/456 |
| 2007/0160646 A1 | 7/2007 | Isozaki et al. | |
| 2009/0292118 A1 | 11/2009 | Lee et al. | |

FOREIGN PATENT DOCUMENTS

| WO | 2009/131631 A1 | 10/2009 |
|---|---|---|
| WO | 2012/017449 A1 | 2/2012 |
| WO | 2012/066502 A1 | 5/2012 |

* cited by examiner

*Primary Examiner* — Bruck Kifle
(74) *Attorney, Agent, or Firm* — Kilpatrick Townsend & Stockton LLP

(57) ABSTRACT

The present invention provides improved processes for obtaining rapamycin derivatives including Biolimus A9.

18 Claims, 3 Drawing Sheets

Sirolimus, R = OH
Everolimus, R = OCH$_2$CH$_2$OH
Biolimus A9, R = OCH$_2$CH$_2$OCH$_2$CH$_3$
Temsirolimus, R = OCOCCH$_3$(CH$_2$OH)$_2$
Zotarolimus, R = NCHN$_3$

LOW TEMPERATURE SYNTHESIS OF RAPAMYCIN DERIVATIVES

CROSS-REFERENCES TO RELATED APPLICATIONS

The present application is continuation of International Application No. PCT/US2014/012398, filed Jan. 21, 2015, which claims priority to U.S. Provisional Application No. 61/755,388, filed Jan. 22, 2013, which applications are incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Biolimus A9® (also known as BA9) is an active pharmaceutical ingredient developed as a drug coating for coronary stents to prevent smooth muscle cell proliferation and restenosis. BA9 is structurally related to rapamycin (also known as sirolimus, CAS [53123-88-9]), a commercially available macrolide natural product synthesized by *Streptomyces hygroscopicus*. Other members of the 'limus' family include everolimus (CAS [159351-69-6]), zotarolimus (CAS [221877-54-9]) and temsirolimus (CAS [162635-04-03]). Members of the family are known to possess immunosuppressive, antifungal, anti-tumor, and/or anti-inflammatory activity in vivo and are useful in the treatment of transplantation rejection, infectious diseases, autoimmune diseases, and conditions characterized by excessive cell proliferation. The chemical structure of BA9 consists of a 31-membered triene macrolide lactone that preserves the core rapamycin ring structure and differs only in the addition of a side chain at position 40 in which the hydroxyl group of rapamycin has been alkylated with an ethoxyethyl group.

The chemical structure of BA9 compared to sirolimus and other sirolimus derivatives is provided in FIG. 1. The structure consists of the rapamycin 31-membered macrolide triene lactone ring with ethoxyethylation at position 40. BA9, like sirolimus, binds to the intracellular immunophilin protein FKBP12. It is believed that the resulting macrolide/FKBP-12 complex then binds, in a manner similar to sirolimus, to mTOR, a protein critical for cell cycle progression. Inactivation of mTOR results in suppression of several specific signal transduction pathways and arrest of the cell cycle at the G1 to S phase.

Given the therapeutic value of BA9 and other rapamycin derivatives, improved processes for preparation of this family of active agents is needed. The present invention addresses this and other needs.

BRIEF SUMMARY OF THE INVENTION

The present invention provides a method for obtaining a compound having the structure of Formula I:

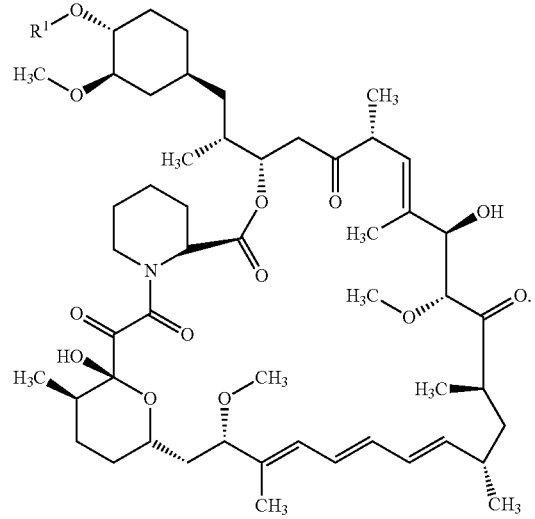

The method includes:
a) combining in a reaction mixture an organic solvent, an organic base compound having a nitrogen heteroatom, a compound having the structure of Formula II

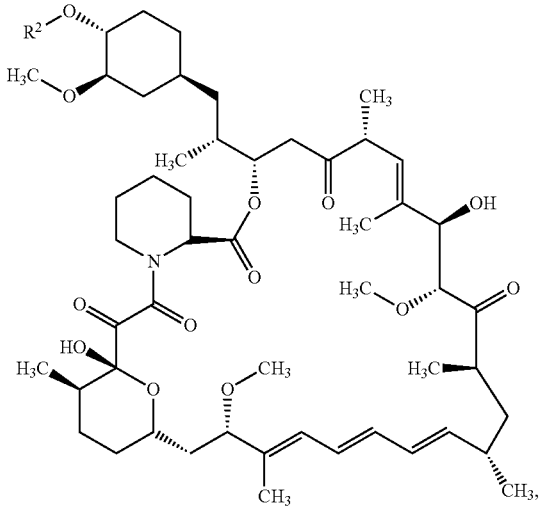

and
a compound having the structure of Formula III

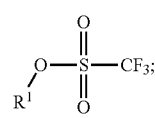

b) maintaining the reaction mixture at a temperature of from about 25° C. to about 55° C.; and
c) separating from the reaction mixture a compound having the structure of Formula I;

wherein

R$^1$ is selected from the group consisting of R$^a$—(O)$_d$—R$^b$, wherein

R$^a$ is C$_{1-5}$alkylene and R$^b$ is C$_{1-5}$alkyl; C$_{1-5}$alkylene-OH;

C$_{6-10}$arylC$_{1-5}$alkyl; C$_{6-10}$arylC$_{1-5}$alkoxy;

C$_{1-5}$alkoxyC$_{1-5}$alkyl; acyl; acylC$_{1-5}$alkyl; aminoC$_{1-5}$alkyl;

C$_{1-5}$alkylaminoC$_{1-5}$alkyl; acylaminoC$_{1-5}$alkyl;

C$_{1-5}$alkoxycarbonylaminoC$_{1-5}$alkyl; and C$_{6-10}$aryl;

R$^2$ is hydrogen; and subscript d is an integer selected from 0-1;

thereby obtaining a compound having the structure of Formula I.

DETAILED DESCRIPTION OF THE INVENTION

I. General

Figure 1:
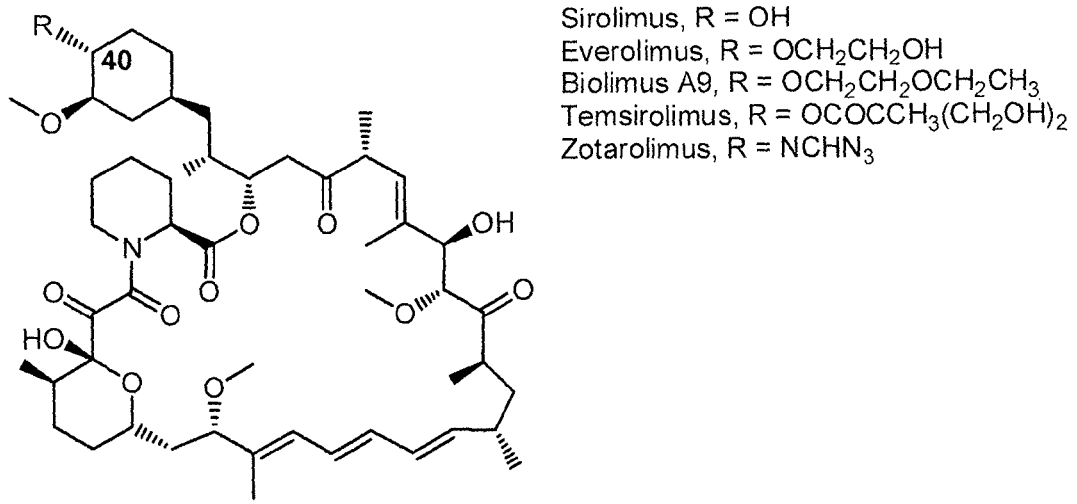
FIG. 1 shows the chemical structures of sirolimus, Biolimus A9, and related derivatives.
Figure 2:
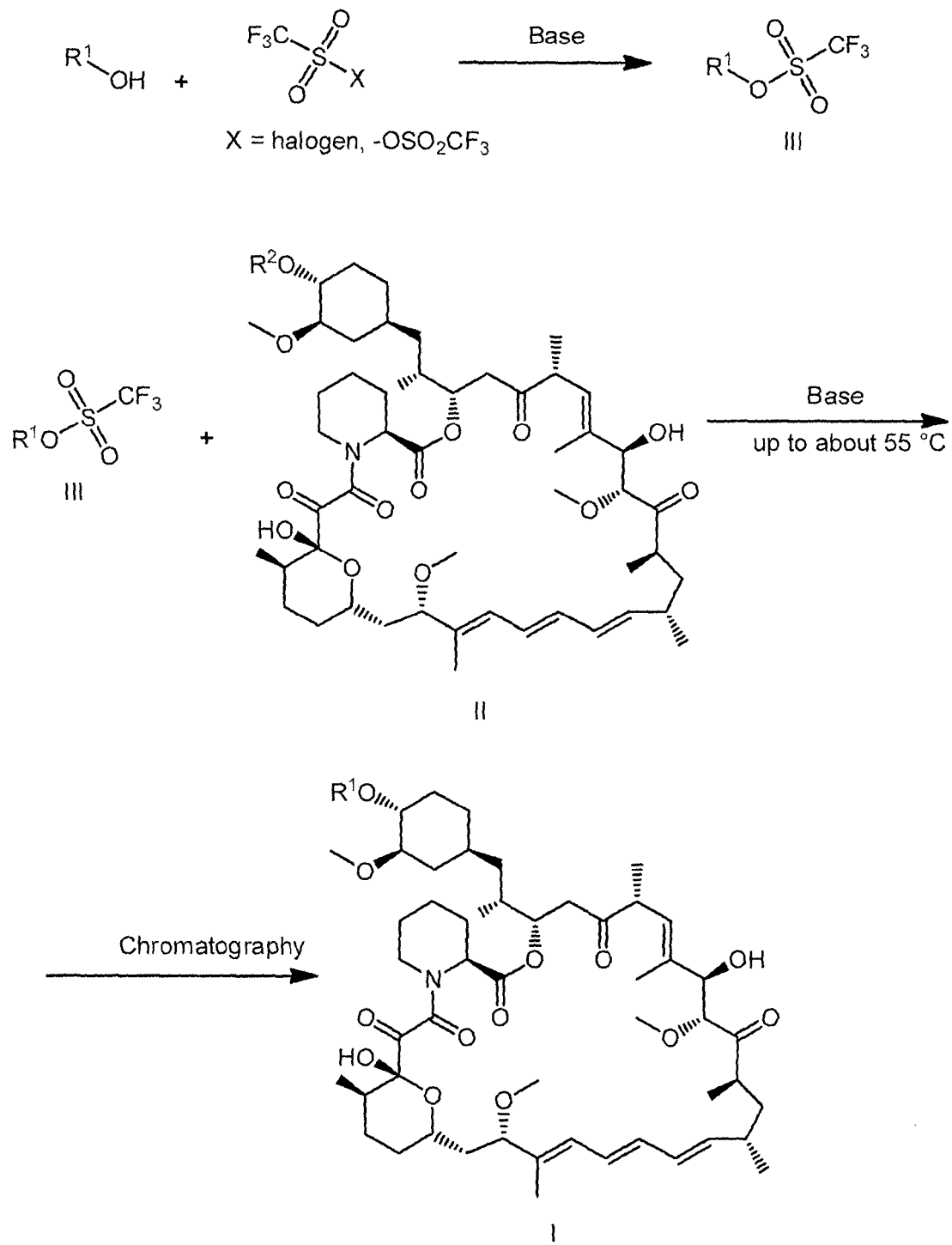
FIG. 2 shows a synthetic scheme for the preparation of rapamycin derivatives according to the methods of the invention.

The present invention provides improved methods for obtaining rapamycin derivatives including Biolimus A9 (BA9). A general scheme for rapamycin derivatization to obtain compounds of Formula I is shown in FIG. 2. The process includes reaction of rapamycin with a suitable triflate at a controlled temperature, followed by work-up and isolation of the products. The various steps of the process are described herein.

Previously described methods of synthesizing 40-O-derivatives of rapamycin were determined to produce undesired by-products having modifications at reactive hydroxyl groups. These by-products, having similarly non-polar properties to the desired derivatives, significantly reduce yield and complicate purification. Surprisingly, it has been found that by controlling the temperature of synthesis, dramatic reductions in the production of by-products can be achieved. Small changes in reaction conditions lead to surprisingly high gains in product yield and purity. These unexpected advantages are described in detail below.

II. Definitions

"Combining in a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Organic solvent" refers to a carbon-containing substance that is liquid at ambient temperature and pressure and is substantially free of water. Examples of organic solvents include, but are not limited to, toluene, methylene chloride, ethyl acetate, acetonitrile, tetrahydrofuran, benzene, chloroform, diethyl ether, dimethyl formamide, dimethyl sulfoxide, and petroleum ether.

"Organic base compound" refers to a carbon-based molecule that is capable of accepting a proton (i.e., a hydrogen cation) to form a conjugate acid of the base. In general, the organic base compounds used in the methods of the invention include at least one nitrogen heteroatom. Examples of organic base compounds include, but are not limited to, Huenig's base (i.e., N,N-diisopropylethylamine), lutidines including 2,6-lutidine (i.e., 2,6-dimethylpyridine), triethylamine, and pyridine.

"Separating" refers to the process of isolating at least a portion of a compound from a mixture containing the compound and at least one other substance. The isolated compound is substantially free of at least one of the other substances present in the mixture.

"Alkyl" refers to a straight or branched, saturated, aliphatic radical having the number of carbon atoms indicated. Alkyl can include any number of carbons, such as C$_{1-2}$, C$_{1-3}$, C$_{1-4}$, C$_{1-5}$, C$_{1-6}$, C$_{1-7}$, C$_{1-8}$, C$_{1-9}$, C$_{1-10}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$ and C$_{5-6}$. For example, C$_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkenyl" refers to a straight chain or branched hydrocarbon having at least 2 carbon atoms and at least one double bond. Alkenyl can include any number of carbons, such as C$_2$, C$_{2-3}$, C$_{2-4}$, C$_{2-5}$, C$_{2-6}$, C$_{2-7}$, C$_{2-8}$, C$_{2-9}$, C$_{2-10}$, C$_3$, C$_{3-45}$ C$_{3-5}$, C$_{3-6}$, C$_4$, C$_{4-5}$, C$_{4-6}$, C$_5$, C$_{5-6}$, and C$_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, and 1,3,5-hexatrienyl.

"Alkynyl" refers to either a straight chain or branched hydrocarbon having, at least 2 carbon atoms and at least one triple bond. Alkynyl can include any number of carbons, such as C$_2$, C$_{2-3}$, C$_{2-4}$, C$_{2-5}$, C$_{2-6}$, C$_{2-7}$, C$_{2-8}$, C$_{2-9}$, C$_{2-10}$, C$_3$, C$_{3-4}$, C$_{3-5}$, C$_{3-6}$, C$_4$, C$_{4-5}$, C$_{4-6}$, C$_5$, C$_{5-6}$, and C$_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, and 1,3,5-hexatriynyl.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, isopropoxy, butoxy, 2-butoxy, isobutoxy, sec-butoxy, tert-butoxy, pentoxy, hexoxy, etc.

"Carbonyl" refers to a moiety consisting of a carbon-oxygen double bond (i.e., —C(O)—).

"Acyl" refers to a moiety including a carbonyl group, as described herein, bound to an alkyl group, an alkenyl group, or an alkynyl group, as described herein.

"Molar ratio" refers to the ratio of the number of moles of a first species to the number of moles of a second species or any other additional species.

"Chromatography" refers to the process of separating a compound from one or more other compounds in a mixture by applying the mixture to a stationary phase and eluting the compounds from the stationary phase using a mobile phase. Examples of chromatography include gas chromatography, silica gel chromatography, reverse-phase chromatography, and affinity chromatography. Chromatography can be conducted, for example, to analyze the progress of a chemical reaction, or to purify a substance after chemical synthesis. Material quantities ranging from micrograms to kilograms are typically used for chromatographic separations, although other quantities can also be used.

"Solidifying" refers to the process of causing a compound in a solution to coalesce into a solid form of the substance. The entirety of a compound in a solution, or any fraction thereof, can be caused to solidify. The solid form can be an amorphous or crystalline substance. "Precipitating" refers to solidifying a substance in an amorphous form.

"Solubilizing" refers to the process of dissolving a solid form of a substance in a solvent to form a solution. The entirety of a solid substance, or any fraction thereof, can be caused to dissolve. Undissolved material can be present in the solvent in the form of a suspension.

The term "about," as used herein to modify a numerical value, indicates a close range around that explicit value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

III. Embodiments of the Invention

The methods of the present invention can be used to prepare a number of macrolide derivatives. Macrolides, including those having structures according to Formulas I and II, are polyketide natural products and synthetic analogs characterized by a macrocyclic lactone ring. The methods of the invention are particularly useful for preparation of rapamycin derivatives Biolimus A9 (BA9), everolimus, zotarolimus, and temsirolimus. Other macrolide derivatives can also be prepared using the methods of the invention.

Accordingly, some embodiments of present invention provide a method for obtaining a compound having the structure of Formula I:

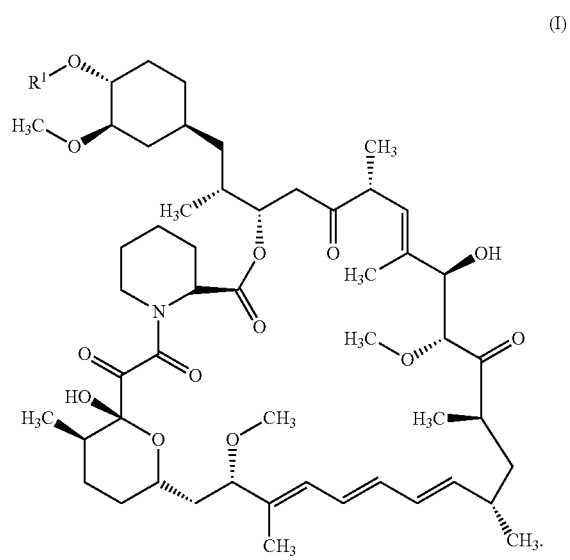

(I)

The method includes:

a) combining in a reaction mixture an organic solvent, an organic base compound having a nitrogen heteroatom, a compound having the structure of Formula II

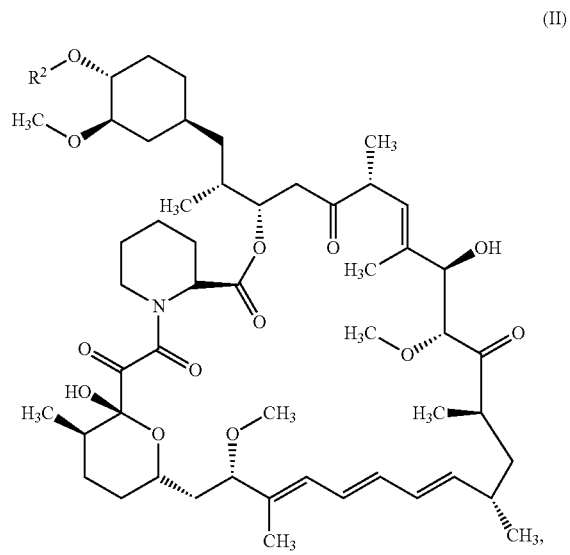

(II)

and a compound having the structure of Formula III

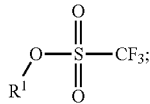

(III)

b) maintaining the reaction mixture at a temperature of from about 25° C. to about 55° C.; and c) separating from the reaction mixture a compound having the structure of Formula I;

wherein $R^1$ is selected from the group consisting of $R^a$—(O)$_d$—$R^b$, wherein $R^a$ is $C_{1-5}$alkylene and $R^b$ is $C_{1-5}$alkyl; $C_{1-5}$alkylene-OH;

$C_{6-10}$aryl$C_{1-5}$alkyl; $C_{6-10}$aryl$C_{1-5}$alkoxy;

$C_{1-5}$alkoxy$C_{1-5}$alkyl; acyl; acyl$C_{1-5}$alkyl; amino$C_{1-5}$alkyl;

$C_{1-5}$alkylamino $C_{1-5}$alkyl; acylamino$C_{1-5}$alkyl;

$C_{1-5}$alkoxycarbonylamino$C_{1-5}$alkyl; and $C_{6-10}$aryl;

$R^2$ is hydrogen; and subscript d is an integer selected from 0-1;

thereby obtaining a compound having the structure of Formula I.

In some embodiments, the reaction mixtures are colorless. In some embodiments, the products of the reactions are colorless. In some embodiments, the invention provides a method for obtaining a compound having the structure of Formula I

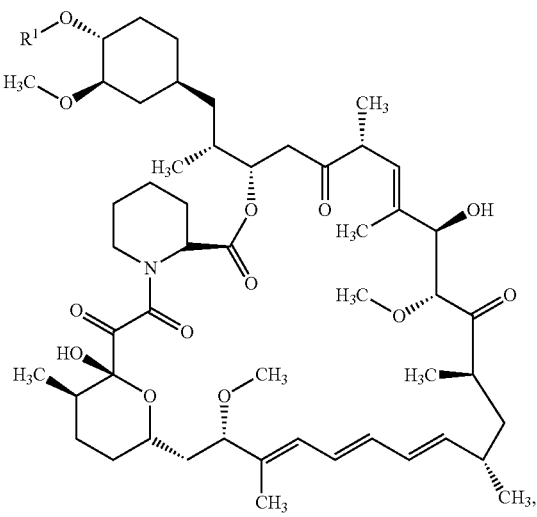

(I)

wherein the method includes:

a) combining in a reaction mixture an organic solvent, an organic base compound having a nitrogen heteroatom, a compound having the structure of Formula II

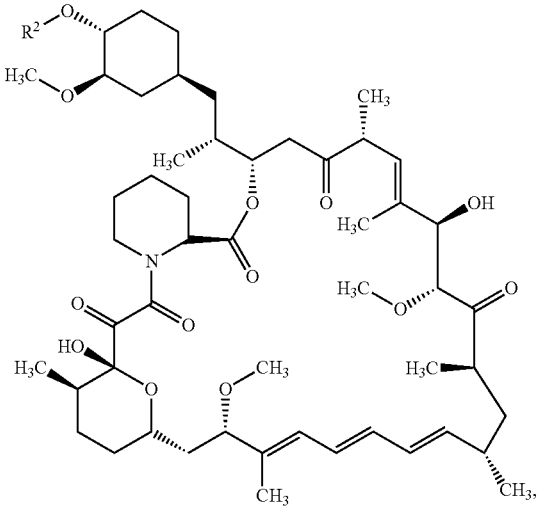

(II)

and a compound having the structure of Formula III

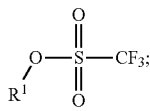

(III)

b) maintaining the reaction mixture at a temperature of from about 25° C. to about 55° C. to yield a colorless reaction mixture; and c) separating from the colorless reaction mixture a compound having the structure of Formula I;

wherein $R^1$ is selected from the group consisting of $R^a$—(O)$_d$—$R^b$, wherein $R^a$ is $C_{1-5}$alkylene and $R^b$ is $C_{1-5}$alkyl; $C_{1-5}$alkylene-OH;

$C_{6-10}$aryl$C_{1-5}$alkyl; $C_{6-10}$aryl$C_{1-5}$alkoxy;

$C_{1-5}$alkoxy$C_{1-5}$alkyl; acyl; acyl$C_{1-5}$alkyl; amino$C_{1-5}$alkyl;

$C_{1-5}$alkylamino$C_{1-5}$alkyl; acylamino$C_{1-5}$alkyl;

$C_{1-5}$alkoxycarbonylamino$C_{1-5}$alkyl; and $C_{6-10}$aryl;

$R^2$ is hydrogen; and subscript d is an integer selected from 0-1;

thereby obtaining a compound having the structure of Formula I.

In some embodiments, the compound having the structure of Formula I is

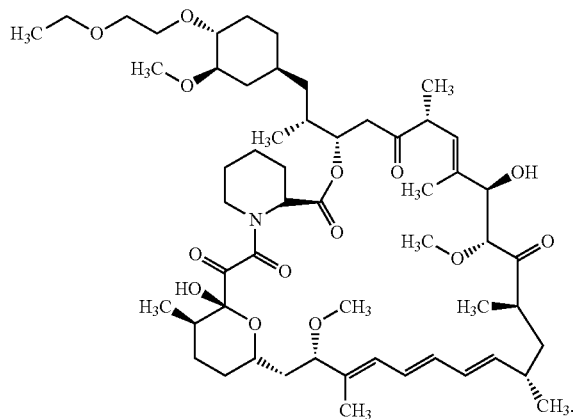

In some embodiments, the compound having the structure of Formula II is rapamycin. In some embodiments, R¹ is CH₂—CH₂—OH. In some embodiments, R¹ is (CH₂)ₑ—O—(CH₂)_f—H, e is an integer selected from 1-5, and f is an integer selected from 1-5. In some embodiments, R¹ is CH₂—CH₂—O—CH₂—CH₃ (i.e., 2-ethoxyethyl). In some embodiments, the sum of e and f is not greater than 7.

In some embodiments, the compound of Formula I is Biolimus A9, also known as: BA9; A9; 40-O-(2-Ethoxyethyl)-rapamycin; 42-O-(2-Ethoxyethyl)-rapamycin; umirolimus; (3S,6R,7E,9R,10R,12R,14S,15E,17E,19E,21S, 23S,26R,27R,34aS)-9,10,12,13,14,21,22,23,24,25,26,27, 32,33,34,34a-Hexadecahydro-9,27-dihydroxy-3-[(1R)-2-[(1S,3R,4R)-4-(2-ethoxyethoxy)-3-methoxycyclohexyl]-1-methylethyl]-10,21-dimethoxy-6,8,12,14,20,26-hexamethyl-23,27-epoxy-3Hpyrido[2,1-c][1,4] oxaazacyclohentriacontine-1,5,11,28,29(4H,6H,31H)-pentone; and (1R,9S,12S,15R,16E,18R,19R,21R,23S,24E, 26E,28E,30S,32S,35R)-1,18-Dihydroxy-12-[(1R)-2-[(1S, 3R,4R)-4-(2-ethoxyethoxy)-3-methoxycyclohexyl]-1-methylethyl]-19,30-dimethoxy-15,17,21,23,29,35-hexamethyl-11,36-dioxa-4-azatricyclo[30.3.1.04,9] hexatriaconta-16,24,26,28-tetraene-2,3,10,14,20-pentaone. Biolimus A9 is also known by CAS No. 851536-75-9.

Any triflate compound suitable for forming compounds of Formula I can be used in the methods of the invention. In general, a triflate used in the methods of the invention has a structure according to Formula III. Triflates having a structure R¹OSO₂CF₃ (i.e., Formula III) can be prepared via the reaction of the corresponding alcohols (R¹OH) with trifluoromethanesulfonic acid, trifluoromethanesulfonyl chloride, trifluoromethanesulfonic anhydride, and the like. While triflates are particularly useful for preparing compounds of Formula I, other derivatives of alcohols R¹OH (including tosylates, mesylates, and brosylates) can also be used in the methods of the invention.

Any suitable organic base can be used in the methods of the invention. In general, bases having a nitrogen heteroatom are used. Examples of suitable bases include Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), 1,5,7-triazabicyclo(4.4.0)dec-5-ene (TBD), 7-methyl-1,5,7-triazabicyclo(4.4.0)dec-5-ene (MTBD), 1,5-diazabicyclo[4.3.0]non-5-ene (DBN), 1,1,3,3-tetramethylguanidine (TMG), 2,2,6,6-tetramethylpiperidine (TMP), pempidine (PMP), 1,4-diazabicyclo[2.2.2]octane (TED), quinuclidine, and the collidines. Combinations of two or more bases can be used. Other bases can also be suitable in the methods of the invention.

In some embodiments, the organic base compound having a nitrogen heteroatom has a structure according to Formula IV

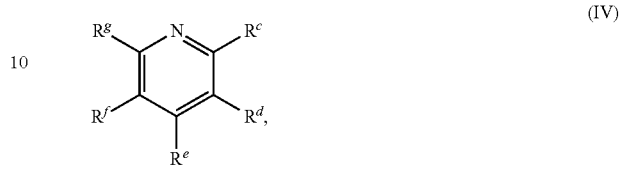

(IV)

wherein $R^c$, $R^d$, $R^e$, $R^f$, and $R^g$ are each independently selected from the group consisting of H, $C_{1-5}$alkyl, OH, and $NH_2$. In some embodiments, the organic base compound having a nitrogen heteroatom is selected from 2,6-lutidine and Huenig's base. In some embodiments, the organic base compound having a nitrogen heteroatom is 2,6-lutidine.

A reaction mixture containing a compound of Formula II, a compound of Formula III, and an organic base can be maintained at a temperature of from about 25° C. to about 55° C. for any length of time sufficient for forming a compound of Formula I. In general, the reaction mixture is maintained at a temperature of from about 25° C. to about 55° C. for anywhere between a few minutes and 24 hours. Maintaining the reaction mixture can be, for example, from about 1 minute to about 24 hours, or from about 30 minutes to about 18 hours, or from about 1 hour to about 12 hours, or from about 2 hours to about 10 hours, or from about 4 hours to about 6 hours. Maintaining the reaction mixture can be about 2, 3, 4, 5, 6, 7, 8, 9, or 10 hours. In some embodiments, the invention provides a method for obtaining a compound having the structure of Formula I as described above, wherein the maintaining in part (b) is for about 2-10 hours.

A reaction mixture containing a compound of Formula II, a compound of Formula III, and an organic base can be maintained at any temperature sufficient for forming a compound of Formula I. In general, the reaction mixture is maintained at a temperature of from about 25° C. to about 55° C. The reaction mixture can be maintained at a temperature of from about 25° C. to about 55° C., or from about 30° C. to about 55° C., from about 35° C. to about 55° C., or from about 40° C. to about 55° C., or from about 45° C. to about 55° C., or from about 50° C. to about 55° C., or from about 30° C. to about 50° C., or from about 35° C. to about 45° C. The reaction mixture can be maintained at about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55° C. In some embodiments, the invention provides a method for obtaining a compound having the structure of Formula I as described above, wherein the maintained temperature in part (b) is from about 25 to about 40° C. Small changes in reaction temperature were found to lead to a surprising reduction in the formation of unwanted byproducts, as discussed in detail below.

In some embodiments, the reaction mixtures of this invention are colorless. In some embodiments, the products of the reactions are colorless. "Colorless reaction mixture" means that the reaction mixture has an optical density of less than 0.5 at a wavelength of between 560-600 nm. The optical density can be, for example, less than 0.5, or less than 0.4, or less than 0.3, or less than 0.2, or less than 0.1, or less than 0.05. Optical density is defined by $$A_\lambda = \log_{10}(I_0/I_1),$$

where $A_\lambda$ is the absorbance at a certain wavelength of light ($\lambda$), $I_1$ is the intensity of the radiation (light) that has passed through the material (transmitted radiation), and $I_0$ is the intensity of the radiation before it passes through the material (incident radiation). The optical density can be measured using an undiluted reaction mixture, or using a sample of the reaction mixture that is diluted with a suitable solvent, such as toluene and the like. "Colorless product" means that a solution of the product in a suitable solvent, such as toluene and the like, has an optical density of less than 0.5 at a wavelength of between 560-600 nm.

Any suitable organic solvent can be used in the methods of the invention. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. In some embodiments, the organic solvent is toluene or methylene chloride. The quantity of solvent is not critical, provided that is sufficient to convert a compound of Formula II to a compound of Formula I. In general, the ratio of the solvent to the compound of Formula II is from about 1:1 to about 1000:1 by weight. The ratio of the solvent to the compound for Formula II can be, for example, about 100:1 or about 10:1 by weight.

Any amount of a compound of Formula III sufficient for forming a compound of Formula I can be used in the methods of the invention. In general, a reaction mixture formed in the methods of the invention includes up to about 60 molar equivalents of a compound of Formula III for each equivalent of a compound of Formula II. The molar ratio of the compound having the structure of Formula III to the compound having the structure of Formula II can be, for example, from about 30 to 1 to about 60 to 1. The molar ratio of the compound having the structure of Formula III to the compound having the structure of Formula II can be about 30 to 1, or about 35 to 1, or about 40 to 1, or about 45 to 1, or about 50 to 1, or about 55 to 1, or about 60 to 1. In some embodiments, the molar ratio of the compound having the structure of Formula III to the compound having the structure of Formula II is from about 30 to 1 to about 60 to 1. Other molar ratios can be suitable in the methods of the invention.

Any amount of organic base sufficient for forming a compound of Formula I can be used in the methods of the invention. In general, a reaction mixture formed in the methods of the invention includes up to about 120 molar equivalents of an organic base for each equivalent of a compound of Formula II. The molar ratio of the organic base compound having a nitrogen heteroatom to the compound having the structure of Formula II can be, for example, from about 80 to 1 to about 120 to 1. The molar ratio of the organic base compound having a nitrogen heteroatom to the compound having the structure of Formula II can be about 80 to 1, or about 85 to 1, or about 90 to 1, or about 95 to 1, or about 100 to 1, or about 105 to 1, or about 110 to 1, or about 115 to 1, or about 120 to 1. In some embodiments, the molar ratio of the organic base compound having a nitrogen heteroatom to the compound having the structure of Formula II is from about 80-120 to 1. In some embodiments, the ratio is 104 to 1. Other molar ratios can be suitable in the methods of the invention. The organic base compound having a nitrogen heteroatom can be added in one portion, or in two or more separate portions. In some embodiments, the organic base compound having a nitrogen heteroatom is added in two separate portions.

The methods of the invention generally include separating a compound of Formula I from the reaction mixture. The compound of Formula I can be separated from one or more compounds such as a solvent, an organic base compound, a compound of Formula II, or a compound of Formula III. Any suitable separation technique can be used to separate the compound of Formula I. Suitable separation techniques include, but are not limited to, filtration of a solidified compound of Formula I, centrifugation of a solidified compound of Formula I, distillation, liquid extraction, sublimation, and chromatographic techniques. Examples of chromatographic techniques include, but are not limited to, normal-phase column chromatography, reverse-phase column chromatography, and thin-layer chromatography. Two or more separation techniques can be conducted in combination to separate the compound of Formula I. In some embodiments, separating the compound having the structure of Formula I comprises using chromatography to separate the compound having the structure of Formula I. In some embodiments, the chromatography is selected from the group consisting of column chromatography, silica gel column chromatography, high-pressure liquid chromatography, and thin layer chromatography. In some embodiments, the chromatography is silica gel column chromatography, and the chromatography is conducted using a mobile phase comprising one or more solvents selected from the group consisting of ethyl acetate, hexane, and heptane. In some embodiments, the chromatography is silica gel chromatography with hexane and ethyl acetate.

In some embodiments, the method includes optionally solidifying the compound having the structure of Formula I. In some embodiments, solidifying the compound having the structure of Formula I includes a) solubilizing the compound having the structure of Formula I in methanol, and b) precipitating the compound having the structure of Formula I from water, thereby solidifying the compound having the structure of Formula I. Other solvents can also be used for solubilizing the compound having the structure of Formula I prior to precipitation from water.

IV. EXAMPLES

Example 1

Preparation of 2-Ethoxyethyl Triflate 2-ethoxyethyl triflate was synthesized according to the method of U.S. Pat. No. 7,812,155. Methylene chloride (558 g) was transferred to a dry round bottomed flask pre-purged with nitrogen. This was followed by addition of 2-ethoxyethanol (75.0 g) and 2,6-lutidine (89.9 g). The reaction mixture was stirred for 20 minutes while cooling the mixture to between 0 and −10° C. Trifluoromethanesulfonic anhydride (282.4 g) was added drop-wise via addition funnel to the reaction mixture. Water was then added to the stirred reaction mixture, and the resulting biphasic mixture was stirred for an additional 5 minutes. The dichloromethane layer was washed, separated, and collected. The methylene chloride solution was dried over sodium sulfate, the sodium sulfate was removed by filtration, and the solvent was removed under reduced pressure at 30° C.

The synthesis was also conducted on 505 g scale of the starting 2-ethoxyethanol. The synthesis followed by purification by vacuum distillation of this batch generated 1060 g (86% yield) of 2-ethoxyethyl triflate. The triflate can also be prepared via methods described in U.S. Pat. No. 7,220,755 and U.S. Pat. No. 7,193,078.

Example 2

Preparation of Biolimus A9 at 55° C.

Coupling of 2-ethoxyethyl triflate (44.3 equivalents) and rapamycin (1.0 equivalent) in toluene with 2,6-lutidine (49.1 equivalents) was conducted at 55° C. (external water bath temperature) for 90 minutes. In this process (on a 2.0 g scale of, rapamycin), the 2-ethoxyethyl triflate was added to a pre-heated reaction mixture (55° C.) in one portion. After heating for 90 minutes, the external heating was turned off followed by addition of the second portion of 2,6-lutidine (54.9 equivalents). After the addition of the second lutidine portion, the reaction mixture was stirred for an additional 90 minutes at ambient temperature followed by workup to isolate crude BA9. The work-up included: 1. dilution of the reaction mixture with ethyl acetate; 2. quench of the reaction mixture with cold 1 N HCl; and 3. wash of the organic layer with three portions of 20% sodium chloride solution in water. The pH of the water layer after the last sodium chloride wash was ~6. The crude material was then purified by an isocratic silica gel column chromatography using only one solvent mixture (n-hexane/ethyl acetate in ratio of 4:6 (vol/vol)).

The process was conducted on a 2.0 g scale. After the internal temperature of the reaction mixture reached 50° C. ($t_{bath}$=51-52° C.), 2-ethoxyethyl triflate was added to the reaction mixture in portions. An increase of the internal temperature up to 58° C. upon the addition was observed. The progress of the reaction was monitored by HPLC. The relative amounts of rapamycin, BA9 and of the main by-product with RRT=1.2 obtained by HPLC analysis are summarized in Table 1. Relative amounts in the tables are expressed as AUC % (area under the curve), i.e., the fraction of the total signal that corresponds to a single peak (corresponding, in turn, to a single species, or two or more species with similar/identical retention times) in a given chromatogram. RRT refers to the ratio of the retention time of a given species to the retention time of BA9 (e.g., for Species X, RRT=$RT_X/RT_{BA9}$). Because the reaction mixture contains toluene and lutidine, the AUC % values are approximate.

TABLE 1

Relative amounts (HPLC/AUC %) of the three main components of the reaction mixture heated by a water bath ($t_{bath}$ = 51-55° C.) at various times of the reaction progress.

| Time (min) | Rapamycin AUC % | BA9 AUC % | By-product (RRT = 1.2) AUC % |
|---|---|---|---|
| 15 | 40.9 | 52.6 | 6.4 |
| 45 | 22.2 | 65.2 | 12.6 |
| 65 | 21.4 | 64.8 | 13.9 |
| 90 | 14.0 | 67.9 | 18.1 |
| +90* | 13.9 | 67.1 | 16.4 |

*90 minutes stirring after addition of the second portion of 2,6-lutidine

As revealed by the data shown in Table 1, the AUC % of BA9 reached its maximum upon 45 minutes of heating. After this time, rapamycin is still consumed, but is also accompanied by an increase of the by-product with RRT of 1.2. Addition of the second portion of 2,6-lutidine followed by stirring at ambient temperature for 90 minutes did not have a significant effect on the composition of the reaction mixture.

HPLC analysis showed that the process resulted in crude BA9 (58.6 AUC content). In addition to unreacted rapamycin (RRT~0.52-0.58), the crude product contained a major impurity/byproduct at HPLC retention time=11.0 mins (RRT=1.2) of 9.6% AUC and a set of impurities between 13.2 (RRT=1.42) and 13.6 minutes (RRT=1.47) up to 1.8% AUC.

Example 3

Preparation of Biolimus A9 at Low Temperatures

The process was conducted at temperatures close to room temperature by the following procedure. The addition of 2-ethoxyethyl triflate (done portion-wise within 1 hour) raised the internal temperature of the initial reaction mixture from 22.6° C. to 26.3° C. After completion of the addition of the triflate, the reaction mixture was stirred at ~26° C. for 40 minutes and then analyzed by HPLC (see entry for 0 hrs in Table 2). The internal temperature of the reaction mixture was then increased within a couple of minutes to 30° C. and the mixture was then stirred at this temperature for up to 19.5 hours. Upon stirring for 19.5 hours, the reaction reached an equilibrium point.

TABLE 2

Relative amounts (HPLC/AUC %) of the three main components of the reaction mixture at various times and internal temperatures of the reaction progress.

| Time (min) | Rapamycin AUC % | BA9 AUC % | By-product (RRT = 1.2), AUC % | Absolute AUC % of BA9 |
|---|---|---|---|---|
| 0 hrs | 67.9 | 31.4 | 0.8 | 30.3 |
| 1.5 hrs at 30° C. | 46.7 | 51.8 | 1.4 | 48.3 |
| 3.5 hrs at 30° C. | 36.2 | 61.4 | 2.3 | 56.9 |
| 5 hrs at 30° C. | 32.0 | 66.1 | 1.9 | 60.7 |
| 19.5 hrs at 30° C. | 27.4 | 69.3 | 3.2 | 64.3 |

For data in Table 2, "BA9 AUC %" refers to the integrated BA9 peak relative to the sum of the BA9, rapamycin, and RRT=1.2 peaks. "Absolute AUC %" refers to the integrated BA9 peak relative to all integrated peaks in the HPLC chromatogram. The data in the Table 2 reveal the following: a) controlling the temperature of the batch during the addition of 2-ethoxyethyl triflate at ≤30° C. contributes significantly to the reduction of the formation of the byproduct with RRT=1.2; b) there is still 32% of unreacted rapamycin in the reaction mixture even after 5 hours at 30° C.; c) it would require in total up to 20 hours of heating to lower the amount of rapamycin to 27 AUC %; and d) the prolonged heating causes an increase of the RRT=1.2 byproduct to 3.2% AUC.

The process was conducted at a maximum temperature of 40° C. In this test, the addition of 2-ethoxyethyl triflate (done portion-wise within 1 hour) raised the internal temperature from 24.2° C. to 27.6° C. After completion of the addition of the triflate, the reaction mixture was stirred at ~27° C. for 30 minutes, then analyzed by HPLC (see entry for 0 hrs in Table 3). The internal temperature of the reaction mixture was then increased to 40° C. and stirred at this temperature for up to 4 hours. As is evident from Table 3, the maximum yield of BA9 in the reaction mixture was reached after 3-4 hours stirring at 40° C.

The comparison of the data for different reaction temperatures indicates the formation of the byproduct with HPLC/RRT=1.2 at higher levels (7-10% AUC) at 40° C.

than for analogous entries at 30° C. (1-2% AUC). Also, it was confirmed that controlling the batch temperature during the addition of 2-ethoxyethyl triflate at ≤30° C. contributes significantly to the reduction of the formation of the byproduct with RRT=1.2 (~1 AUC % content).

The synthesis of crude BA9 at temperatures ≤40° C. with full work-up of the reaction mixture generating crude BA9 was tested on 2.0 g scale of rapamycin. Upon portion-wise addition of 2-ethoxyethyl triflate within 30 mins, the internal temperature raised from 20.0° C. to 24.0° C. and upon further stirring (still without external heating) to 25.5° C. (after 1 hour from the start of the triflate addition). The reaction mixture was then heated externally to 40° C. (within 25 minutes) and stirred at this temperature for 3 hours. After the initial reaction, 12.9 g of 2,6-lutidine was added to the reaction mixture. The new reaction mixture was stirred at 30° C. for 90 minutes.

TABLE 3

Relative amount (HPLC/AUC %) of the three main components of the reaction mixture at various times and internal temperatures of the reaction progress.

| Time (min) | Rapamycin AUC % | BA9 AUC % | By-product (RRT = 1.20), AUC % | Absolute AUC % of BA9 |
|---|---|---|---|---|
| 0 hrs | 59.7 | 39.1 | 1.2 | 37.7 |
| 1 hrs at 40° C. | 32.8 | 59.9 | 6.5 | 57.5 |
| 2 hrs at 40° C. | 26.9 | 65.2 | 7.9 | 60.3 |
| 3 hrs at 40° C. | 22.8 | 68.6 | 8.6 | 62.2 |
| 4 hrs at 40° C. | 20.6 | 70.0 | 9.5 | 62.9 |

Figure 3A:
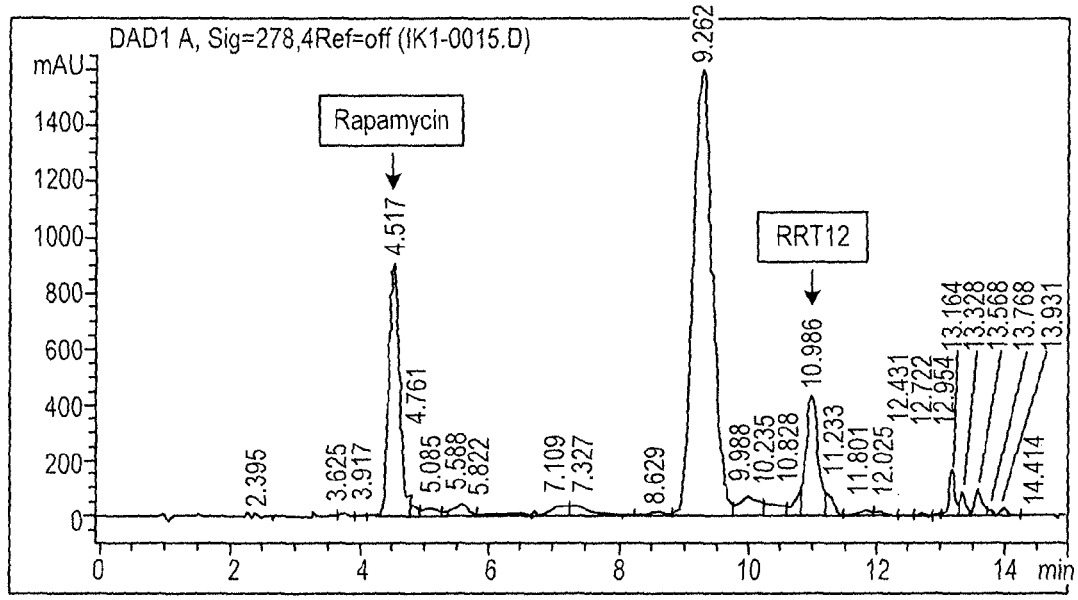
FIG. 3A shows the HPLC analysis of crude BA9 synthesized at 50-55° C.
Figure 3B:
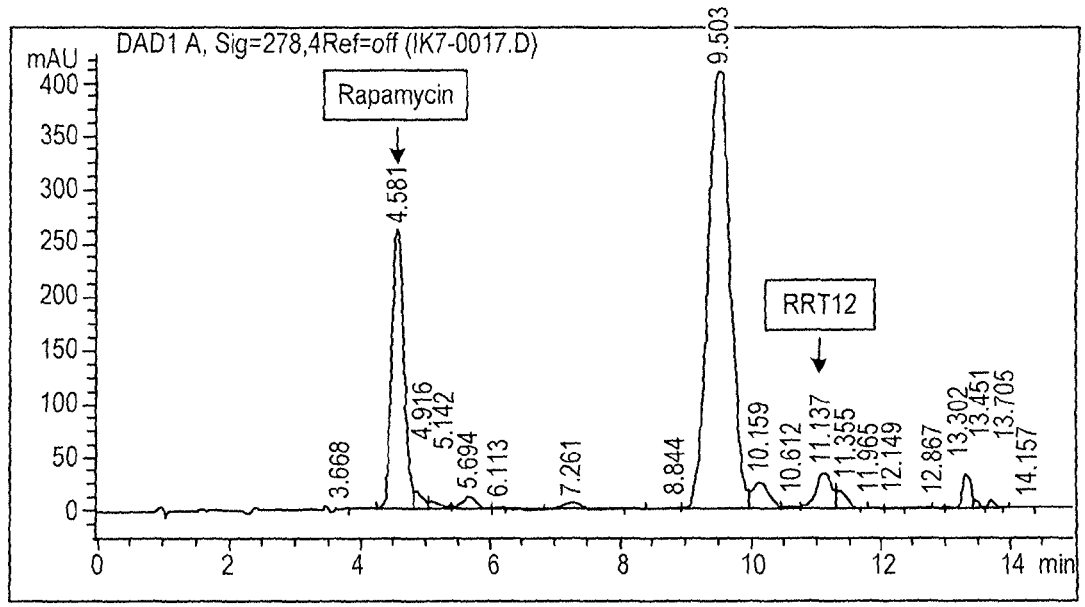
FIG. 3B shows the HPLC analysis of crude BA9 synthesized at 40° C.

Work-up of the product included: 1. dilution of the reaction mixture with 160 mL of ethyl acetate; 2. quench of the reaction mixture with 160 mL of cold 1 N HCl in the temperature range between 3° C. and 9° C.; and 3. wash of the organic layer with three portions of 20% sodium chloride solution in water (320 mL, 200 mL and 200 mL, respectively). The pH of the water layer after the last sodium chloride wash was 6. The HPLC trace of the oily product of the crude product revealed a higher content of BA9 (66.3 AUC %). HPLC analysis showed that the content of BA9 in analogous crude product generated at 50-55° C. was only 58.6%. Moreover, the comparison of the two lots of crude BA9 (generated at 40° C. and at 50-55° C.) reveals lesser amounts of byproducts in the lot generated at the lower temperature. The most striking is the difference in the content of the byproduct with HPLC/RRT=1.2 in the two lots. While the content of this impurity is 9.6 AUC % for the lot synthesized at the higher temperature (see FIG. 3A), the content is only 3.6 AUC % for the crude product generated at 40° C. (see FIG. 3B).

Example 4

Reaction Scale-Up

Because the distribution of product and by-product was found to depend on the temperature of the reaction mixture, the temperature profile for the rapamycin derivatization process was investigated on various scales. The process was conducted on a 30.0 g-scale with respect to starting rapamycin. Upon portion-wise addition of 2-ethoxyethyl triflate within 30 mins, the internal temperature raised from 20° C. to 27° C. and upon further stirring (still without external heating) to 32° C. (after 1 hour from the start of the triflate addition). The reaction mixture was then heated externally to 40° C. and stirred at this temperature for 3 hours. After the initial reaction, 2,6-lutidine was added to the reaction mixture and stirred at 30° C. for 90 minutes. The work-up of the reaction mixture provided an oily product. Based on the HPLC analysis, the crude product generated first time by the large scale synthesis contained 64.2 AUC % of BA9 and 4.9% of the byproduct with RRT=1.2.

The scale-up synthesis of BA9 according to the process described in the above paragraph was repeated two more times, in both cases at 52.0 g scale of starting rapamycin. The further increase of the scale of the synthesis contributed to an even larger exotherm of the batch upon addition of 2-ethoxyethyl triflate (from 20 to 36° C. in the first case, and from 18 to 33° C. in the second case). As evident from the HPLCs of the crude Biolimus A9 synthesized at 52 g scale, the crude products contain 62.9 and 65.0 AUC % of Biolimus A9 and 10.2 and 8.5 AUC % of the by-product with RRT of 1.20.

Comparison of the initial exotherm observed during the addition of 2-ethoxyethyl triflate to the reaction mixture at different scales of the synthesis shows that the extent of this exothermic effect is proportional to the scale of the synthesis (see the comparison of the temperature increases due to the exothermic process for previously described syntheses in Table 4).

The comparison of the impurity profiles of the crude Biolimus A9 at a 2 g scale in the first instance and of the lots of crude Biolimus A9 synthesized at 30-52 g reveal the formation of larger amounts of the byproduct with RRT=1.2 upon the scale-up of the synthetic procedure. While the amount of this impurity was only 3.6% for a 2 g synthesis product, the amount of this impurity was found to be 4.9-10.2 AUC % for the products synthesized at the large scale. Without wishing to be bound by any particular theory, it is believed that this difference is caused by a lower batch temperature increase during the thermally uncontrolled addition of the 2-ethoxyethyl triflate on a small scale (temperature raised to 25.5° C., while at the large scale synthesis up to 36° C.; refer to Table 4). As such, measures to control reaction temperature should be adjusted depending on the scale of the reaction.

TABLE 4

Relationship between the scale of the synthesis of crude BA9 and extent of the temperature increase due to the exotherm associated with addition of triflate to reaction mixture.

| Scale of synthesis (amount of starting rapamycin) | Observed temperatures | Temperature increase |
|---|---|---|
| 2 g | 20.0° C. to 25.5° C. | 5.5° C. |
| 30 g | 20° C. to 32° C. | 12° C. |
| 52 g | 20° C. to 36° C. | 16° C. |
| 52 g | 18° C. to 33° C. | 15° C. |

Example 5

Work-Up of Biolimus A9

The synthesis was repeated on 2.0 g scale of rapamycin, with the maximal reaction temperature of only 35° C. The only difference was a slow ramping of the increase of the temperature of the reaction mixture from 25° C. to 35° C. (within 30 minutes, instead of ~5 minutes, to further minimize the amounts of byproducts). The synthesis again generated crude Biolimus A9 with a high HPLC/AUC content (66.8%) of the API and with a low content of the byproduct with RRT=1.2 (RT=10.7 min, 2.7%).

The crude product was purified using silica gel chromatography employing a gradient solvent mixture of n-hexane and ethyl acetate. The chromatographic fractions were analyzed by HPLC. Fractions with HPLC/AUC % of BA9≥95.0% and simultaneously passing the specifications for the presence of the known and unknown impurities were combined. This provided 40% yield of purified BA9 with HPLC/AUC purity=96.2%.

Besides the main portion of purified BA9, two other significant portions of purified BA9 were obtained from the silica gel chromatography purification: a) 12% yield of a portion with HPLC/AUC purity of 91.8% and b) 8% yield of a portion with HPLC/AUC purity of 91.8%.

The use of a shallow gradient and extended elution with hexane/ethyl acetate resulted in a poor resolution of the impurities during column chromatography on a larger scale (52 g scale of rapamycin). A steeper gradient was used with a mixture of n-hexane/ethyl acetate. The purification of raw Biolimus A9 by the steeper gradient silica gel column chromatography resulted in 23.5 g of purified product (HPLC/AUC % purity of 96.0%) starting from 52 g of rapamycin. An additional 10.0 g of product (HPLC/AUC purity of 94.9%) was obtained.

Example 6

Small Changes in Reaction Temperature Lead to Surprising Increases in Product Distribution Small temperature changes were seen to result in a surprising shift in the product/by-product distribution. The comparison of reaction mixture samplings for synthesis at 60° C. versus 55° C., as shown in Table 5 and Table 6, indicates that the small reduction in reaction temperature dramatically reduces the formation of byproducts. This was most apparent for the compound eluting at retention time 11.5 minutes, a disubstituted impurity (12.5% RT 11.5 reacted at 60° C. versus 5.9% at 55° C.).

TABLE 5

Sampling of reaction mixture containing rapamycin, dichloromethane, Huenig's base and 2-ethoxyethyltriflate run for 80 min at 60° C.

| | Rap (AUC %) | BA9 (AUC %) | Impurity (RT 11.5) | Impurity (RT 12.0) | Impurity (RT 12.4) | Impurity (RT 13.6) |
|---|---|---|---|---|---|---|
| Rapamycin in DCM in presence of Huenig's base | 98.0% | — | — | — | — | — |
| 2 min after addition of triflate | 92.9% | 5.0% | — | — | — | 0.6% |
| After reaction mixture reaches 60° C. | 90.6% | 8.2% | 0.1% | — | 0.2% | — |
| 17 min at 60° C. | 49.6% | 41.7% | 2.2% | 0.1% | 0.8% | 0.7% |
| 35 min at 60° C. | 53.8% | 37.4% | 2.5% | 0.4% | 0.6% | 0.6% |
| 52 min at 60° C. | 37.9% | 45.3% | 5.6% | 1.3% | 1.2% | 0.8% |
| 65 min at 60° C. | 38.1% | 38.4% | 7.1% | 2.1% | 1.6% | 0.7% |
| 75 min at 60° C. | 28.6% | 38.0% | 10.5% | 3.1% | 1.9% | 1.1% |
| 80 min at 60° C. | 29.8% | 34.6% | 10.0% | 2.9% | 2.2% | 0.7% |
| FINAL Crude cooled to 9° C. | 20.7% | 39.8% | 12.5% | 3.9% | 2.9% | 1.4% |

Correspondingly, there is improved conversion of the rapamycin starting material to BA9 by running the reaction for the same duration at a temperature of only 5° C. lower (39.8% BA9 reacted at 60° C. versus 70.2% at 55° C.). The suppression of by-product formation is particularly advantageous because the by-products are especially difficult to remove from the product mixtures. In contrast, unreacted starting materials are easy to remove. As such, the methods described herein significantly increase the yield of purified product and reduce the cost and complications associated with previously known methods.

TABLE 6

Sampling of reaction mixture containing rapamycin, dichloromethane, Huenig's base and 2-ethoxyethyltriflate run for 80 min at 55° C.

| | Rap (AUC %) | BA9 (AUC %) | Impurity (RT 11.5) | Impurity (RT 12.0) | Impurity (RT 12.4) | Impurity (RT 13.6) |
|---|---|---|---|---|---|---|
| Rapamycin in DCM in presence of Huenig's base | — | — | — | — | — | — |
| 2 min after addition of triflate | — | — | — | — | — | — |

TABLE 6-continued

Sampling of reaction mixture containing rapamycin, dichloromethane,
Huenig's base and 2-ethoxyethyltriflate run for 80 min at 55° C.

| | Rap (AUC %) | BA9 (AUC %) | Impurity (RT 11.5) | Impurity (RT 12.0) | Impurity (RT 12.4) | Impurity (RT 13.6) |
|---|---|---|---|---|---|---|
| After reaction mixture reaches 55° C. | 90.4% | 7.7% | 0.1% | — | 0.2% | |
| 15 min at 55° C. | 57.1% | 37.2% | 1.6% | — | 0.6% | 0.6% |
| 30 min at 55° C. | 42.9% | 56.5% | 2.6% | — | 0.7% | 1.3% |
| 45 min at 55° C. | 35.8% | 53.9% | 3.8% | — | 1.0% | 1.3% |
| 65 min at 55° C. | 16.8% | 67.8% | 4.8% | — | 1.0% | 2.0% |
| 80 min at 55° C. | 28.4% | 57.6% | 4.6% | 0.2% | 0.7% | 1.0% |
| FINAL Crude cooled to 5° C. | 15.1% | 70.2% | 5.9% | — | 1.1% | 2.6% |

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for obtaining a compound having the structure of Formula I

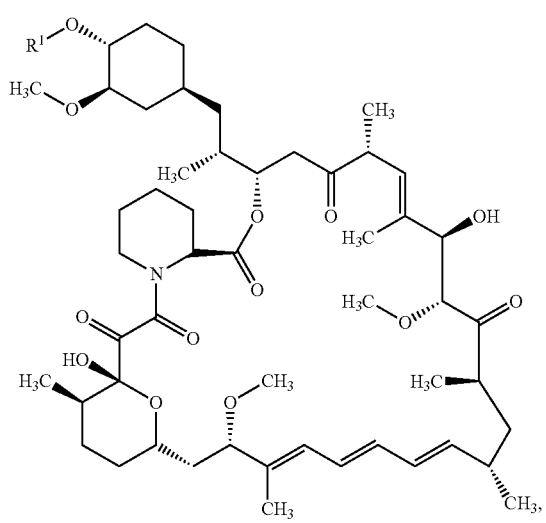

the method comprising:
a) combining in a reaction mixture an organic solvent, an organic base compound having a nitrogen heteroatom, a compound having the structure of Formula II

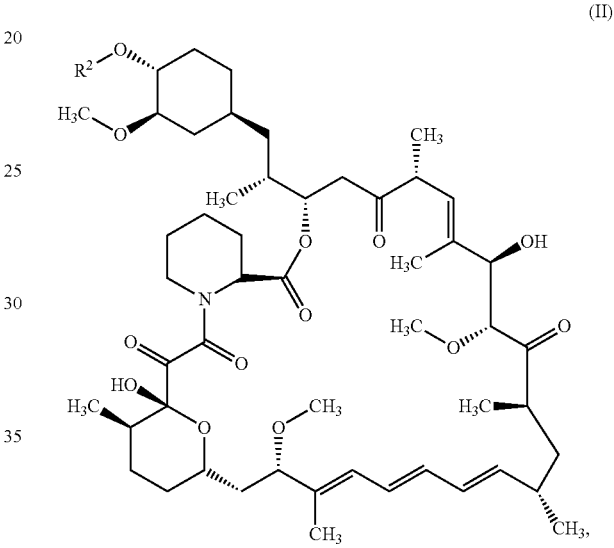

and
a compound having the structure of Formula III

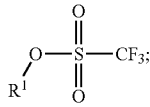

b) maintaining the reaction mixture at a temperature of from 25° C. to 55° C.; and
c) separating from the reaction mixture a compound having the structure of Formula I;
wherein
$R^1$ is $(CH_2)_e$—O—$(CH_2)_f$—H;
e is an integer selected from 1-5;
f is an integer selected from 1-5; and
$R^2$ is hydrogen;
thereby obtaining a compound having the structure of Formula I.

2. The method of claim 1, wherein the compound having the structure of Formula I is

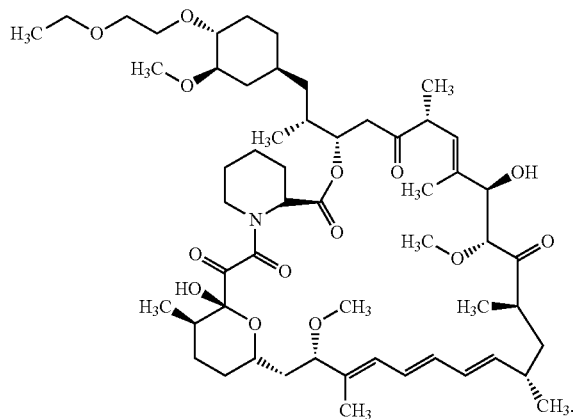

3. The method of claim 1, wherein $R^1$ is $CH_2$—$CH_2$—O—$CH_2$—$CH_3$.

4. The method of claim 1, wherein the organic base compound having a nitrogen heteroatom has the structure of Formula IV

(IV)

wherein:

$R^c$, $R^d$, $R^e$, $R^f$, and $R^g$ are each independently selected from the group consisting of H, $C_{1-5}$alkyl, OH, and $NH_2$.

5. The method of claim 1, wherein the organic base compound having a nitrogen heteroatom is selected from 2,6-lutidine and N,N-diisopropylethylamine.

6. The method of claim 1, wherein the organic base compound having a nitrogen heteroatom is 2,6-lutidine.

7. The method of claim 1, wherein the maintaining in part (b) is for 2-10 hours.

8. The method of claim 7, wherein the maintained temperature in part (b) is from 25 to 40° C.

9. The method of claim 1 wherein the organic solvent is toluene or methylene chloride.

10. The method of claim 1, wherein the molar ratio of the compound having the structure of Formula III to the compound having the structure of Formula II is from 30 to 1 to 60 to 1.

11. The method of claim 1, wherein the molar ratio of the organic base compound having a nitrogen heteroatom to the compound having the structure of Formula II is from 80 to 1 to 120 to 1.

12. The method of claim 11, wherein the ratio is 104 to 1.

13. The method of claim 1, wherein the organic base compound having a nitrogen heteroatom is added in two separate portions.

14. The method of claim 1, wherein separating the compound having the structure of Formula I comprises using chromatography.

15. The method of claim 14, wherein the chromatography is selected from the group consisting of silica gel column chromatography, high-pressure liquid chromatography, and thin layer chromatography.

16. The method of claim 15, wherein the chromatography is silica gel column chromatography, and wherein the chromatography is conducted using a mobile phase comprising one or more solvents selected from the group consisting of ethyl acetate, hexane, and heptane.

17. The method of claim 1, further comprising solidifying the compound having the structure of Formula I.

18. The method of claim 17, wherein solidifying the compound having the structure of Formula I comprises
    a) solubilizing the compound having the structure of Formula I in methanol; and
    b) precipitating the compound having the structure of Formula I from water;
    thereby solidifying the compound having the structure of Formula I.

* * * * *